United States Patent [19]

Phillips et al.

[11] Patent Number: 5,599,559
[45] Date of Patent: Feb. 4, 1997

[54] CALCIUM CHANNEL BLOCKING POLYPEPTIDE FROM AGELENOPSIS APERTA AND THERAPEUTIC METHODS EMPLOYING IT

[75] Inventors: Douglas Phillips, Gales Ferry; Mary E. Kelly, Groton; Nicholas A. Saccomano, Ledyard; Robert A. Volkmann, Mystic, all of Conn.

[73] Assignee: Pfizer Inc., New York, N.Y.

[21] Appl. No.: 379,550

[22] PCT Filed: Jun. 10, 1993

[86] PCT No.: PCT/US93/05392

§ 371 Date: Apr. 27, 1995

§ 102(e) Date: Apr. 27, 1995

[87] PCT Pub. No.: WO94/02511

PCT Pub. Date: Feb. 3, 1994

Related U.S. Application Data

[63] Continuation of Ser. No. 919,538, Jul. 27, 1992, abandoned.

[51] Int. Cl.⁶ .......................... A61K 35/56; A61K 38/17; C07K 14/435
[52] U.S. Cl. .................. 424/538; 514/12; 514/21; 530/324

[58] Field of Search ............... 530/324; 435/69.1; 514/12, 21; 424/538

[56] References Cited

U.S. PATENT DOCUMENTS

| | | | |
|---|---|---|---|
| 5,064,657 | 11/1991 | Jackson et al. | 424/537 |
| 5,122,596 | 6/1992 | Phillips et al. | 530/350 |
| 5,196,204 | 3/1993 | Jackson et al. | 424/538 |
| 5,281,693 | 1/1994 | Jackson et al. | 530/324 |

FOREIGN PATENT DOCUMENTS

| | | | |
|---|---|---|---|
| 0425096A1 | 5/1991 | European Pat. Off. | C07K 15/08 |

OTHER PUBLICATIONS

Adams, M. E., et al. (1990) *J. Biol. Chem.* 265: 861–867.
Venema, V. J., et al. (1992) *J. Biol. Chem.* 267:2610–2615.

*Primary Examiner*—David L. Fitzgerald
*Attorney, Agent, or Firm*—P. C. Richardson; P. H. Ginsburg; B. C. Zielinski

[57] ABSTRACT

A polypeptide isolated from the venom of the *Agelenopsis aperta* spider blocks calcium channels in cells of various organisms and is useful in blocking such calcium channels in cells per se, in the treatment of calcium channel-mediated diseases and conditions, and in the control of invertebrate pests.

3 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Agelenopsis aperta
        ( F ) TISSUE TYPE: venom ( x i ) SEQUENCE DESCRIPTION: SEQ ID NO:1:

Glu Ala Cys Ala Gly Ala Tyr Lys Ser Cys Asp Lys Val Lys Cys Cys

-continued

```
     1                     5                          10                          15
    His  Asp  Arg  Arg  Cys  Arg  Cys  Asn  Ile  Ala  Met  Asp  Asn  Cys  Val  Cys
                   20                        25                        30
    Lys  Leu  Phe  Tyr  Cys  Glu  Leu  Phe  Gly  Thr  Cys  Asp  Arg  Leu  Lys  Pro
                   35                        40                        45
```

CALCIUM CHANNEL BLOCKING POLYPEPTIDE FROM AGELENOPSIS APERTA AND THERAPEUTIC METHODS EMPLOYING IT

This application is a continuation of application Ser. No. 07/919,538, filed 27 Jul. 1992 and now abandoned.

BACKGROUND OF THE INVENTION

This invention relates to a polypeptide found in the venom of the *Agelenopsis aperta* spider and to a polypeptide having substantially the same amino acid sequence and substantially the same activity as said polypeptide. The polypeptides and the pharmaceutically acceptable salts thereof block calcium channels in cells including neuronal and muscle cells of various organisms including invertebrates and vertebrates. This invention also relates to the use of said polypeptides and their salts in blocking calcium channels in cells such as cells in the nervous and muscular system of an organism, per se, and in the treatment of calcium channel mediated diseases and conditions in a mammal. Further, this invention relates to compositions comprising said polypeptides and salts thereof.

Compounds which are calcium antagonists have a variety of utilities. Calcium antagonists can find clinical application in the treatment of such conditions as angina, hypertension, cardiomyopathies, supraventricular arrhythmias, aesophogeal achalasia, premature labor and Raynaud's disease among others. See W. G. Nayler, *Calcium Antagonists*, Academic Press, Harcourt Brace Jovanovich Publishers, New York, N.Y. 1988, the teachings of which are incorporated herein by reference. Further, such compounds are useful in the study of the physiology of cells such as neuronal and muscle cells.

Other polypeptides isolated from *Agelenopsis aperta* are disclosed in U.S. Pat. No. 5,122,596.

SUMMARY OF THE INVENTION

This invention concerns a polypeptide found in the venom of the *Agelenopsis aperta* spider. The polypeptide of this invention and the fraction in which it is present according to this invention are as follows.

Agelenopsis peptide $J_2$ has the following amino acid sequence, SEQ ID NO: 1.

$H_2$N-Glu-Ala-Cys-Ala-Gly-Ala-Tyr-Lys-Ser-Cys-Asp-Lys-Val-Lys-Cys-Cys-His-Asp-Arg-Arg-Cys-Arg-Cys-Asn-Ile-Ala-Met-Asp-Asn-Cys-Val-Cys-Lys-Leu-Phe-Tyr-Cys-Glu-Leu-Phe-Gly-Thr-Cys-Asp-Arg-Leu-Lys-Pro

The polypeptide of this invention blocks calcium channels in cells. Accordingly, this polypeptide is useful in blocking calcium channels in cells, per se. This polypeptide is also useful in the control of invertebrate pests and in the treatment of diseases and conditions in a mammal mediated by calcium channel function in cells.

Also within the scope of this invention are polypeptides which have substantially the same amino acid sequence and substantially the same calcium channel blocking activity as the polypeptide described above.

This invention also concerns pharmaceutical compositions comprising said polypeptides and methods of administering said polypeptides.

DETAILED DESCRIPTION OF THE INVENTION

Venom is obtained from the *Agelenopsis aperta* spider through the process of milking by electrical stimulation according to standard methods well known to those skilled in the art. It is preferred that the method employed is one which safeguards against contamination of the whole venom by abdominal regurgitant or hemolymph. Such methods are well known to those skilled in the art. The whole venom so obtained is stored in a frozen state at about −78° C. until used for purification as described below. Purification of the constituents from the whole venom is accomplished by reverse phase high performance liquid chromatography (HPLC) on a variety of preparative and semi-preparative columns such as C-4 and C-18 Vydace® columns (Rainin Instrument Co. Inc., Mack Road, Woburn Mass. 01801 ). Peak detection is carried out monochromatically at 220–230 nm. Further analysis of the fractions can be accomplished with, for example, polychrome UV data collected with a Waters 990 diode array detector (Millipore Corporation, Waters Chromatography Division, 34 Maple Street, Milford, Mass. 01757). The fractions from the columns are collected by known methods such as through the use of an ISCO/ "FOXY" fraction collector and an ISCO 2159 peak detector (ISCO, 4700 Superior, Lincoln, Nebr. 68504). The fractions are collected in appropriately sized vessels such as sterile polyethylene laboratoryware. Concentration of the fractions is then accomplished by lyophilization from the eluant followed by lyophilization from water. Purity of the resulting constituent fractions then can be determined by chromatographic analysis using an analytical column with a gradient system which is more isocratic than the system used in the final purification of the fractions.

The polypeptide of the invention can be sequenced according to known methods. A general strategy for determining the primary structure includes, for example, the following steps. 1) Reduction and S-pyridylation of disulfide-bridged cysteine residues to enhance substrate susceptability to enzymatic attack. 2) Controlled cleavage of the peptide through single or multi-step enzymatic digestion. 3) Isolation and purification of peptide fragments via reverse phase high performance liquid chromatography (HPLC). 4) Characterization of peptide fragments through N-terminal sequencing and ion-spray mass spectrometry.

S-pyridylethylation of cysteine residues of the polypeptides under study can be performed, for example, in solution followed by amino acid sequencing of the polypeptides. One such procedure for S-pyridylethylation can be accomplished as described below.

About 1 to 10 µg of polypeptide is dissolved or diluted in up to 50 µl of a buffer prepared by mixing 1 part 1M TrisHCl, pH 8.5, containing 4 mM EDTA and 3 parts 8M guanidine-HCl. 2.5 µl of 10% aqueous 2-mercaptoethanol is added and the mixture is incubated at room temperature in the dark under argon for two hours. After incubation, 2 µl of 4-vinylpyridine (fresh reagent stored under argon at −20° C.) is added and the mixture is incubated for another two hours at room temperature in the dark under argon. The mixture is then desalted, preferably by chromatography on a short, reverse phase column. The recovered alkylated polypeptide is then sequenced according to known methods.

Given the benefit of the disclosure herein with respect to the peptide present in fraction $J_2$ of venom from *Agelenopsis aperta*, it is now possible to obtain said peptide by methods other than through isolation/purification from whole venom. The polypeptides of this invention can be produced using recombinant DNA techniques through the cloning of a coding sequence for said polypeptides or portions thereof. For example, hybridization probes which take advantage of the now known amino acid sequence information of said polypeptide can be employed according to methods well known to those skilled in the art to clone a coding sequence for the entire polypeptide. A combination of recombinant DNA techniques and in vitro protein synthesis can also be employed to produce the polypeptides of this invention. Such in vitro protein synthesis methods include, but are not limited to, use of an ABI 430A solid phase peptide synthesizer (Applied Biosystems, Inc., 850 Lincoln Center Drive, Foster City, Calif. 94404) employing standard Merrifield chemistry or other solid phase chemistries well known to those skilled in the art.

It is well known in the art that certain amino acid substitutions can be made in polypeptides which do not affect, or do not substantially affect, the function of said polypeptides. The exact substitutions which are possible vary from polypeptide to polypeptide. Determination of permissible substitutions is accomplished according to procedures well known to those skilled in the art. Thus, all polypeptides having substantially the same amino acid sequence and substantially the same calcium channel blocking activity are within the scope of this invention.

The polypeptides of this invention block calcium channels present in a variety of cells such as cells in the nervous and muscular system of invertebrates and vertebrates.

The ability of the polypeptides of this invention to block calcium channels is demonstrated by the following procedure. Cerebellar granule cells are prepared from the cerebellum of 8 day old rats (Wilkin et al., *Brain Res*, 115, 181–199, 1976). Squares (1 cm$^2$) of Aclar (Proplastics Inc., 5033 Industrial Ave., Wall, N.J. 07719) are coated with poly-L-lysine and placed in 12-well dishes that contain 1 ml of Eagles Basal Medium. The cells are dissociated and aliquots containing 6.25×10$^6$ cells are added to each well containing the squares of Aclar. Cytosine-beta-D-arabino furanoside (final concentration 10 µM) is added 24 hours after plating. The cells are used for fura2 analysis at 6, 7 and 8 days of culture. The cells (attached to the Aclar squares) are transferred to 12 well dishes containing 1 ml of 2 µM fura2/AM (Molecular Probes Inc., Eugene, Oreg. 97402) in HEPES buffer (containing 0.01% bovine serum albumin, 0.01% dextrose, pH 7.4, magnesium-free). The cells are incubated for 40 minutes at 37° C.; the fura2/AM-containing buffer is removed and replaced with 1 ml of the same buffer without fura2/AM. To a quartz cuvette is added 2.0 ml of prewarmed (37° C.) buffer. The cells on the Aclar are placed in the cuvette and the cuvette is inserted in a thermostatted (37° C.) holder equipped with a magnetic stirrer and the fluorescence is measured with a fluorescence spectrophotometer (Biomedical Instrument Group, University of Pennsylvania). The fluorescence signal is allowed to stabilize for about two minutes. Then 5–20 µl of a stock solution of the compound under study in phosphate buffered saline (PBS, pH 7.4) at appropriate concentration is added to the cuvette. Calibration of the fluorescent signals and fura2/AM leakage correction are performed using the established procedures of Nemeth et al., *J. Biol. Chem.*, 262, 5188 (1987) at the completion of each test. The maximum fluorescence value (Fmax) is determined by addition of ionomycin (35 µM) and the minimum fluorescence value (Fmin) is determined by the subsequent addition of EGTA (12 mM) to chelate calcium. Employing the foregoing procedure, calcium channel blocking by a subject polypeptide is shown to occur by a decrease in fluorescence upon addition of the subject polypeptide. The polypeptide of the invention exhibits low IC$_{50}$ values, under 200 nm, for blocking calcium channels using this assay. For comparison, two known commercial calcium channel antagonists, Nifedipine and Verapamil, have IC$_{50}$ values of 33 nm and 4800 nm, respectively.

The polypeptides of this invention are useful as calcium channel blockers in cells, per se. As such, these polypeptides are also useful in the control of invertebrate pests and in the treatment of diseases and conditions mediated by calcium channels function in cells in a mammal such as angina, hypertension, cardiomyopathies, supraventricular arrhythmias, aesophogeal achalasia, premature labor and Raynaud's disease. Further, these polypeptides are useful in the study of the physiology of cells including, but not limited to, cells of the nervous and muscular system.

Also within the scope of this invention are the pharmaceutically acceptable salts of the polypeptides of this invention. Such salts are formed by methods well known to those skilled in the art. For example, base salts of the polypeptides can be prepared according to conventional methods.

When a polypeptide of this invention is to be administered to a mammal, it can be administered alone or in combination with pharmaceutically acceptable carriers or diluents in a pharmaceutical composition according to standard pharmaceutical practice. The polypeptides can be administered orally or parenterally with the parenteral route of administration being preferred for polypeptides. Parenteral administration includes intravenous, intramuscular, intraperitoneal, subcutaneous and topical administration.

For oral use of a polypeptide of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a polypeptide or salt thereof of this invention is used in a human subject, the daily dosage will normally be determined by the prescribing physician. Moreover, the dosage will vary according to the age, weight and response of the individual patient, as well as the severity of the patient's symptoms and the potency of the particular compound being administered.

When a polypeptide or salt thereof of this invention is used in control of invertebrate pests, said polypeptide is administered to said invertebrate directly or provided to the environment of said invertebrate. For example, a compound of this invention can be sprayed as a solution onto said invertebrate. The amount of compound necessary for control of said invertebrate will vary according to the invertebrate and environmental conditions and will be determined by the person applying the compound.

When a polypeptide or salt thereof of this invention is used in the physiological study of cells, said polypeptide is administered to the cells according to methods well known to those skilled in the art. For example, said polypeptide can be administered to cells in an appropriate physiological buffer. An appropriate concentration of a polypeptide of this invention for use in such studies is 200 µM. However, the concentration of said polypeptide in such studies may be greater than or much less than 200 µM. The amount of the polypeptide administered will be determined by the person skilled in the art according to well known methods.

EXAMPLE b 1

A. Crude *Agelenopsis aperta* venom (~40 µl) was applied to a reversed phase HPLC column (VYDAC® C-18, 300 Å, 22×250 mm) operated using a biphasic linear gradient program from 95% A and 5% B to 80% A and 20% B over 30 minutes, then to 30% A and 70% B over 25 minutes (A=0.1% trifluoroacetic acid and B=$CH_3CN$), with detection at 220 nm and a flow rate of 15 ml/minute. The desired fraction was collected from 38.3 to 38.7 minutes. Pooled like fractions from individual runs were concentrated by lyophilization.

B. The material from the fractionation of step A, above, derived from 100 µl of crude venom, was applied to a reversed phase HPLC column (Vydac®, C-18, 300 Å, 22×250 mm) operated using a linear gradient program from 77% A and 23% B to 70% A and 30% B over 25 minutes (A =0.1% trifluoroacetic acid and B=$CH_3CN$) with detection at 220 nm and a flow rate of 12 ml/minute. The desired fraction was collected from 17.3 to 17.7 minutes. Pooled like fractions from individual runs were concentrated by lyophilization.

The structure of peptide $J_2$ was determined and verified by the following methods. PTC amino acid analysis was carried out on 1 to 10 nmols in triplicate using the Waters Pico-Tag system. N-terminal sequencing was carried out on a pulse-liquid sequenator (ABI) both on native and on reduced/ pyridylethylated peptide. The primary structure of the polypeptide was obtained by use of an automated pulse liquid sequencer (Applied Biosystems, model 473A). Mass spectral analysis data was obtained from a BIO-ION plasma desorption time of flight mass spectrometer.

A pyridylethylated derivative of peptide $J_2$ suitable for N-terminal sequencing was prepared in the following fashion. Peptide $J_2$ (50 mg) was dissolved in 10 µl of buffer (1:3 ratio of 1M tris, pH 8.4, 4 µM EDTA-dibasic and 8M guanidine-hydrochloride and was treated with 2 µl of a 0.454M (10% v/v) solution of 2-mercaptoethanol in buffer and kept for 3 hours in the dark at room temperature. The reaction mixture was then treated with 2 µl of a 0.456M solution of 4-vinylpyridine in buffer and kept at room temperature in the dark for 18 hours. The reaction mixture was diluted with 90 µl of water and 40 µl of acetonitrile and applied to an HPLC column (Baker WPC-18, 4.6×250 mm) operated using a biphasic linear gradient program of 80% A and 20% B for 5 minutes followed by 80 to 50% A and 29 to 50% B over 30 minutes (A=0.1% trifluoroacetic acid, B=$CH_3CN$) with detection at 220 nM and a flow rate of 1.0 ml/minute. The desired fraction was collected at 20.8 to 21.3 minutes and was concentrated by lyophilization.

The data taken together affirm the structure of peptide $J_2$ as shown below.

SEQ ID NO: 1, 48 residues, 10 cysteines, 5 disulfide bonds.
 Calculated mass=5474.4.
 Observed mass=5474.
 Estimated pI=7.98.

---

We claim:

1. A substantially pure polypeptide having the amino acid sequence, SEQ ID NO: 1, or a pharmaceutically acceptable salt thereof.

2. A method of blocking calcium channels in a cell comprising administering to said cell a calcium channel blocking amount of a polypeptide according to claim 1.

3. A method according to claim 2 wherein said cell is in the nervous system of a mammal.

\* \* \* \* \*